(12) United States Patent
Udayampalayam Palanisamy et al.

(10) Patent No.: US 8,293,924 B2
(45) Date of Patent: Oct. 23, 2012

(54) PROCESS FOR THE PREPARATION OF CARBAPENEM ANTIBIOTIC

(75) Inventors: Senthilkumar Udayampalayam Palanisamy, Chennai (IN); Mohan Singaravel, Chennai (IN); Vignesh Babu Heeralal, Dindigul (IN)

(73) Assignee: Orchid Chemicals & Pharmaceuticals Limited, Chennai (IN)

( * ) Notice: Subject to any disclaimer, the term of this patent is extended or adjusted under 35 U.S.C. 154(b) by 29 days.

(21) Appl. No.: 12/733,817

(22) PCT Filed: Sep. 30, 2008

(86) PCT No.: PCT/IB2008/002560
§ 371 (c)(1),
(2), (4) Date: Jun. 11, 2010

(87) PCT Pub. No.: WO2009/047604
PCT Pub. Date: Apr. 16, 2009

(65) Prior Publication Data
US 2010/0311984 A1     Dec. 9, 2010

(30) Foreign Application Priority Data
Oct. 8, 2007  (IN) .............................. 2259/CHE/2007

(51) Int. Cl.
*C07D 487/02*     (2006.01)
(52) U.S. Cl. ..................................................... 548/453
(58) Field of Classification Search ................. 548/453
See application file for complete search history.

(56) References Cited

U.S. PATENT DOCUMENTS

| | | |
|---|---|---|
| 4,260,543 A | 4/1981 | Miller |
| 4,374,772 A | 2/1983 | Hazen et al. |
| 4,616,038 A | 10/1986 | Kahan et al. |
| 5,286,856 A * | 2/1994 | Kaneko et al. ................ 540/350 |
| 6,111,098 A | 8/2000 | Inoue et al. |
| 7,078,534 B2 | 7/2006 | Kumar et al. |
| 7,241,885 B2 | 7/2007 | Kumar et al. |
| 2002/0095034 A1 | 7/2002 | Zenoni et al. |
| 2005/0004359 A1 | 1/2005 | Rai et al. |
| 2010/0010214 A1 | 1/2010 | Kikuchi et al. |
| 2010/0240886 A1* | 9/2010 | Nishino et al. ............... 540/350 |

FOREIGN PATENT DOCUMENTS

| | | |
|---|---|---|
| WO | WO 02/094773 A2 | 11/2002 |
| WO | WO 03/042215 A1 | 5/2003 |
| WO | WO 2008/062279 A2 | 5/2008 |

OTHER PUBLICATIONS

International Search Report issued in corresponding International Application No. PCT/IB2008/002560, mailed Feb. 6, 2009.
Written Opinion of the International Searching Authority issued in corresponding International Application No. PCT/IB2008/002560, mailed Feb. 6, 2009.
Connolly et al., "Freeze Crystallization of Imipenem," Journal of Pharmaceutical Sciences, vol. 85, No. 2, Feb. 1996, pp. 174-177.

* cited by examiner

*Primary Examiner* — Joseph McKane
*Assistant Examiner* — Samantha Shterengarts
(74) *Attorney, Agent, or Firm* — Oliff & Berridge, PLC

(57) ABSTRACT

An improved process for the preparation of carbapenem antibiotic of formula (I) or its hydrate is provided.

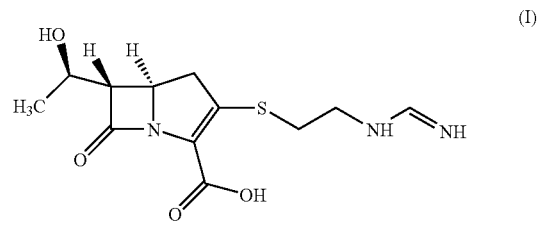

5 Claims, No Drawings

PROCESS FOR THE PREPARATION OF CARBAPENEM ANTIBIOTIC

FIELD OF THE INVENTION

An improved process for the preparation of the carbapenem antibiotic of formula (I) or its hydrate is described.

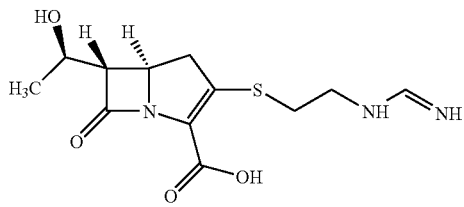

(I)

The compound of the formula (I) is known as Imipenem and exhibits broad-spectrum antibiotic activity. The chemical name of Imipenem is: (5R,6S)-6-[(1R)-1-hydroxyethyl]-3-[[2-[(iminomethyl)amino]ethyl]thio]-7-oxo-1-azabicyclo[3.2.0]hept-2-ene-2-carboxylic acid monohydrate. Imipenem in combination with Cilastatin sodium is marketed in US as PRIMAXIN®.

BACKGROUND OF THE INVENTION

Imipenem is a broad spectrum β-lactam antibiotic, belonging to the group carbapenems. It is derived from a compound called thienamycin of formula (II).

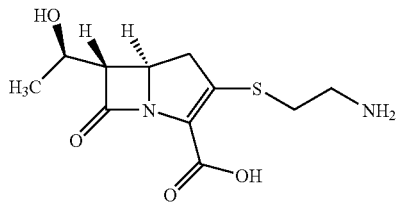

(II)

Imipenem and the process for its preparation are described in U.S. Pat. No. 4,194,047 patent, in which the process involves lyophilization. Methyl formimidate was reacted with thienamycin in the process for the preparation of N-formimidoylthienamycin (Imipenem).

U.S. Pat. No. 4,260,543 patent describes crystalline Imipenem monohydrate. According to this patent, crystalline Imipenem monohydrate is prepared by dissolving N-formimidoylthienamycin in water followed by diluting the said solution with ethanol to yield crystalline N-formimidoylthienamycin monohydrate (Imipenem) crystals. This patent provides the technique of crystallization of Imipenem in aqueous medium by the addition of an organic solvent.

U.S. Pat. No. 4,374,772 patent describes a process for preparing Imipenem by reacting thienamycin with benzyl formimidate as shown in reaction scheme-1.

Reaction Scheme-1

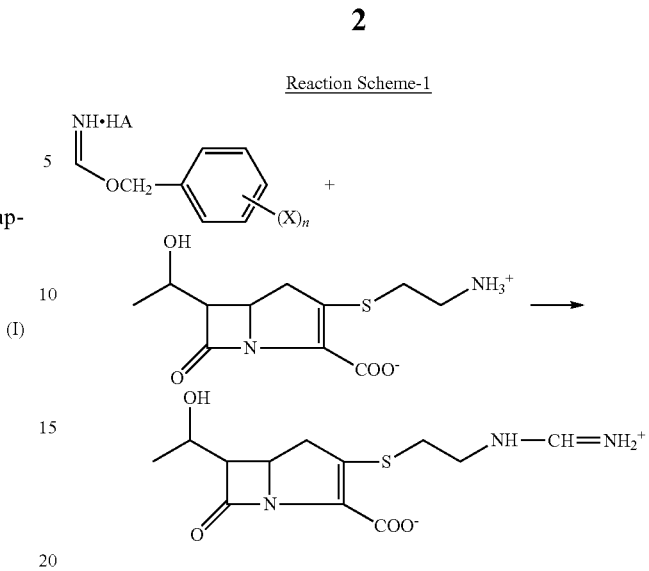

The reagent benzyl formimidate utilized in the preparation of Imipenem is obtained by reacting formamide (such as dibutylformamide or dimethyl formamide), benzyl alcohol and benzoyl chloride in a solvent selected from 2-methyltetrahydrofuran, tetrahydrofuran, diethyl ether, isopropyl ether, sulfolane, dioxane and the like, preferably, 2-methyltetrahydrofuran; in the presence or absence of catalyst selected from (R)-tetrahydro-1-methyl-3,3-diphenyl-1H,3H-pyrrolo 1,2-C or tetrahydro-1-methyl-3,3-diphenyl-1H,3H-pyrrolo-[1,2-C][1,3,2]oxazaborole-borane complex or (S)-tetrahydro-1-methyl-3,3-diphenyl-1H,3H-pyrrolo-[1,2-C][1,3,2]oxazaborole-borane complex at a temperature in the range of −25° C. to −20° C. The product was recovered by the addition of acetic anhydride according to the literature available in the prior art.

U.S. Pat. No. 4,616,038 patent provides a process for the crystallization of N-formimidoylthienamycin by adding ethanol to a concentrated solution of N-formimidoylthienamycin. This patent provides a method for isolating Imipenem monohydrate directly from the reaction solution with out using lyophilization method.

US 2002/0095034 describes a process for the preparation of Imipenem by activating (3R,5R,6S)-2-oxo-6-[(1R)-1-hydroxyethyl]carbapenem-3-carboxylic acid p-nitrobenzyl ester with diphenylphosphorohydrochloride followed by reacting the activated compound with cysteamine hydrochloride in the presence of a base to produce thienamycin p-nitrobenzyl ester hydrochloride in the form of N-methylpyrrolidinone solvate, which is further reacted with alkyl formimidate to produce Imipenem p-nitrobenzyl ester, followed by deprotection to produce Imipenem.

U.S. Pat. No. 7,241,885 B2 patent (Indian patent application number: 595/DEL/2001) provides a process for the preparation and isolation of pure crystalline Imipenem monohydrate by crystallizing Imipenem monohydrate from a solution thereof which contains an organic solvent, aqueous solvent, or a mixture thereof, without using lyophilization.

Process for the preparation of crystalline Imipenem monohydrate is described in U.S. Pat. No. 7,078,534 B2 patent (Indian patent application number: 983/DEL/2000), wherein dianion chromatography is used prior to crystallization of Imipenem monohydrate.

US 2005/004359 A1 (Indian patent application number: 1152/DEL/2001) describes a process for the preparation of crystalline Imipenem monohydrate which comprises: (a) dissolving crude Imipenem monohydrate in warm water in the presence of base; (b) subjecting the resultant solution to activated carbon treatment; and (c) adding an organic solvent to precipitate Imipenem monohydrate as a crystalline product. Due to less solubility of Imipenem monohydrate in water this patent provides a method to dissolve Imipenem monohydrate in water at higher temperature (45-60° C.) in the present of base. At high temperature and pH chances are there for the degradation of Imipenem.

Freeze-crystallization of Imipenem is reported in *Journal of Pharmaceutical Sciences* 1996, 85(2), 174-177. Solutions containing Imipenem and sodium bicarbonate were crystallized from acetone-water solvent system.

The above processes either use freeze-crystallization or lyophilization or chromatography or reverse osmosis, which are not viable for industrial scale-up process.

Color of the reconstituted solution is an important indicator that indicates stability of the product. The formation of intense color like dark brown, black or reddish brown indicates the presence of highly unsaturated, intensely colored impurities and/or degradation products. A significant change in color of the reconstituted solution can become a limiting factor to the shelf life of a parenteral product. In order to get rid of colored impurities, the prior art patents utilize column chromatographic techniques or treatment with activated carbon.

With our continued research for developing a process for the preparation of compound of formula (I), we have identified a process, in which Imipenem monohydrate was dissolved in the presence of suitable inorganic salt, and yielded the to final compound in good quality.

OBJECTIVES OF THE INVENTION

The main objective is to provide a simple and commercially viable, industrially scalable sterile process for the preparation of compound of the formula (I).

Another objective is to provide a simple and commercially viable, industrially scalable process for the purification of compound of formula (I), which avoids chromatographic techniques.

One more objective of the invention is to provide an improved process for the preparation of imipenem monohydrate having good stability.

SUMMARY OF THE INVENTION

Accordingly, the present invention provides an improved process for preparation of sterile Imipenem of the formula (I) or its monohydrate

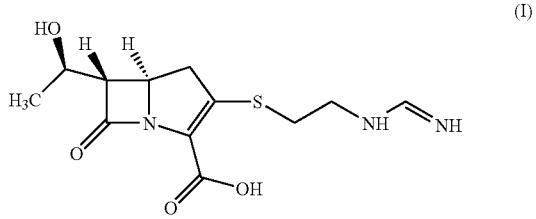

(I)

the said process comprising the steps of:
i) dissolving Imipenem or its hydrate in water in the presence of inorganic salt;
ii) optionally adjusting the pH of the step (i) solution to 6.5-7.8;
iii) treating the solution with carbon and/or decolorizing agent selected from the reagent consisting of silica, alumina, or clay;
iv) optionally seeding with imipenem monohydrate;
v) adding an organic solvent; and
vi) isolating imipenem monohydrate.

DETAILED DESCRIPTION

In an embodiment of the present invention, the inorganic salt used in step (i) is selected from sodium chloride, potassium chloride, lithium chloride and the like. The use of an inorganic salt facilitates the dissolution of Imipenem monohydrate in water. The prior art processes requires high temperature (up to 70° C.) and a base for dissolving Imipenem monohydrate in water. The contact of Imipenem or any carbapenem with base (high pH) at high temperature may tend to degrade the final compound as carbapenem compounds are sensitive towards bases. Accordingly, the use of inorganic salt like sodium chloride for the dissolution of Imipenem is found to be advantages in dissolving Imipenem monohydrate in water and constitutes novelty of the present invention.

In another embodiment of the present invention, the pH of the clear solution is optionally adjusted to 6.5 to 7.8 at 2-15° C., using base selected from N-methylmorpholine, sodium bicarbonate, triethylamine, N,N-diisopropylamine, 1,1,3,3-tetramethylguanidine (TMG), N-methypyrrolidine, sodium hydroxide and the like. Since the pH of the aqueous solution containing Imipenem (Imipenem monohydrate) according to the present invention adjusted at low temperature the degradation is minimized, where as in the prior art process the degradation is found to be high as it involves the prolonged contact of carbapenem with base at higher temperature.

In still another embodiment of the present invention, the aqueous solution thus Obtained was treated with activated carbon and/or decolorizing agent selected from group consisting of silica, alumina, clay or mixtures thereof. Such a treatment with decolorizing agent found to be advantage in terms of increasing stability of the product and color of the reconstituted solution meets the pharmaceutical requirement for an injectable product.

In yet another embodiment of the present invention, decolorizing agent is selected more specifically from activated alumina neutral.

In one more embodiment of the present invention, organic solvents used in step (v) is selected from group comprising lower alcohols such as methanol, ethanol, n-propanol, isopropanol and the like; ketones such as acetone and methyl ethyl ketone or mixture(s) thereof.

In yet another embodiment, a sterile process is provided for the preparation of Imipenem monohydrate by filtering the solution obtained in step (iii) through a series of sterile micron filters and isolating Imipenem monohydrate in sterile area.

In another embodiment of the present invention, the crystalline Imipenem monohydrate obtained has good purity and stability suitable for formulation.

In one more embodiment of the present invention, the present invention provides an improved process for the preparation of carbapenem antibiotic having better color on reconstitution, said process comprising treating the aqueous solution of carbapenem antibiotic with decolorizing agent selected from group consisting of silica, alumina, clay or mixtures thereof. The carbapenem antibiotic includes but not limited, Meropenem or is hydrate; Ertapenem or it sodium salt or its prodrug, Doripenem or is hydrate, Panipenem or its hydrate, Imipenem or its hydrate etc.

The following examples are provided by way of illustration only and should not be construed to limit the scope of the invention.

EXAMPLE-1

Preparation of Imipenem Monohydrate Sterile

To purified water (300 mL) containing sodium chloride (3 g) was added Imipenem monohydrate (5 g) at 38-42° C. The clear solution was cooled to 2-10° C. and the pH was adjusted to 7.0 to 7.2 using N-methylmorpholine. The clear solution was subjected to carbon treatment (0.5 g). Carbon was filtered and the bed washed with water. The filtrate was filtered through 0.2 micron filter paper and seeded with Imipenem monohydrate (optionally added EDTA, Sodium hydrosulphite) and acetone was added slowly. The crystallized product obtained was filtered, washed with aqueous acetone (20 mL) followed by acetone (20 mL) and dried to give Imipenem monohydrate. (Purity: 99.40%).

EXAMPLE-2

Preparation of Imipenem Monohydrate Sterile

To purified water (300 mL) containing lithium chloride (3 g) was added Imipenem monohydrate (5 g) at 38-42° C. The clear solution was cooled to 2-10° C. and the pH was adjusted to 7.0 to 7.2 using N-methylmorpholine. The clear solution was subjected to carbon treatment (0.5 g). Carbon was filtered and the bed washed with water. The filtrate was filtered through 0.2 micron filter paper and seeded with Imipenem monohydrate (optionally added EDTA, Sodium hydrosulphite) and acetone was added slowly. The crystallized product obtained was filtered, washed with aqueous acetone (20 mL) followed by acetone (20 mL) and dried to give Imipenem monohydrate. (Purity: 99.35%).

EXAMPLE-3

Preparation of Imipenem Monohydrate Sterile

To purified water (100 mL) containing sodium chloride (12.5 g) was added imipenem monohydrate (5 g) at 25-30° C. The pH was adjusted to 7.0 to 7.2 using N-methylmorpholine at 25-30° C. and cooled to 5 to 10° C. The clear solution was subjected to carbon treatment (0.5 g). Carbon was filtered and the bed washed with water. The filtrate was filtered through 0.2 micron filter paper and cooled to 2-5° C. and seeded with imipenem monohydrate. To the filtrate was added EDTA, sodium hydrosulphite followed by acetone, the crystallized product obtained was filtered, washed with aqueous acetone followed by acetone and dried to give Imipenem monohydrate. (Purity 99.30%)

EXAMPLE-4

Preparation of Imipenem Monohydrate Sterile

To purified water (100 mL) containing potassium chloride (12.5 g) was added imipenem monohydrate (5 g) at 25-30° C. The pH was adjusted to 7.0 to 7.2 using N-methylmorpholine at 25-30° C. and cooled to 5 to 10° C. The clear solution was subjected to carbon treatment (0.5 g). Carbon was filtered and the bed washed with water. The filtrate was subjected to series of micron filtration in sterile area and cooled to 2-5° C. and seeded with imipenem monohydrate. To the filtrate acetone was added slowly. The crystallized product obtained was filtered, washed with aqueous acetone followed by acetone and dried to give Imipenem monohydrate. (Purity 99.25%)

EXAMPLE-5

Preparation of Imipenem Monohydrate Sterile

To purified water (300 mL) containing sodium chloride (3 g) was added to Imipenem monohydrate (5 g) at 38-42° C. The clear solution was cooled to 2-10° C. and the pH was adjusted to 7.0 to 7.2 using N-methylmorpholine. To the clear solution Was added carbon (0.5 g) and activated alumina (3 g). Carbon and alumina were filtered and the bed washed with water. The filtrate was filtered through 0.2 micron filter paper and seeded with Imipenem monohydrate (optionally added EDTA, Sodium hydrosulphite) and acetone was added slowly. The crystallized product obtained was filtered, washed with aqueous acetone (20 mL) followed by acetone (20 mL) and dried to give Imipenem monohydrate. (Purity: 99.35%).

EXAMPLE-6

Preparation of Ertapenem or it Sodium Salt

To the solution of sodium bicarbonate (2.5 g in 70 mL water) Ertapenem monosodium (15 g) was slowly added at 0-5° C., by maintaining pH around 7.5 using sodium hydroxide solution. The solution obtained was subjected to carbon treatment, followed by stirred with alumina and filtered. To filtrate, containing Ertapenem disodium was filtered through 0.2 micron filter paper and added into 2500 mL of cold IPA solution at 0-5° C. The solid obtained was filtered washed with IPA followed by acetone and IPE, dried under dry and wet nitrogen to yield Ertapenem disodium (Yield—8-12 g; sodium content: 9.2-10.5%; moisture content: 5-7%; pH: 7.5-8.0). The color of the reconstituted product was pale yellow.

EXAMPLE-7

Preparation of Ertapenem or it Sodium Salt

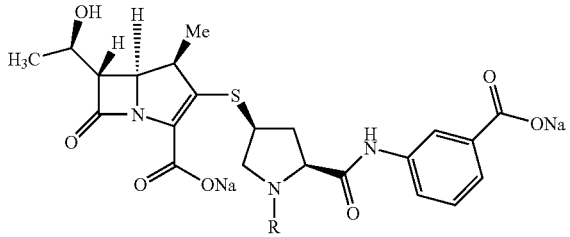

wherein R represents hydrogen or COOM and M represents hydrogen or sodium ion.

To the solution of sodium salt of di-protected Ertapenem (50 g) {prepared by following the process disclosed in WO 2008062279} in a mixture of carbonated water (500 ml), IPA (2.6 ml) and ethyl acetate (20 L) in autoclave were charged sodium bicarbonate (6.5 gm) and Pd/carbon and subjected to hydrogenation with 3 to 10 Kg pressure at 5-10° C. After completion of reaction $CO_2$ gas was purged and the reaction mass was filtered. The aqueous layer was separated, washed with ethyl acetate and was treated with activated carbon and neutral alumina, the residual solvents in aqueous layer removed using degassing technique and filtered. The aqueous layer was filtered through 0.2 micron filter paper and added into isopropyl alcohol and ethanol under stirring. The precipitated amorphous form of Ertapenem disodium (having moisture content: about 7% to 11%) was slurry washed with ethanol and IPE. The obtained solid (having moisture content:

about 2.5% to 6%) was dried using dry $N_2$ gas followed by humidified $N_2$ gas to yield amorphous form of Ertapenem disodium (having moisture content: about 7% to 12%) and again dried using dry $N_2$ gas at about 5-10° C. to yield amorphous form of Ertapenem disodium having moisture content (2.5-4.5%) with pharmaceutically acceptable level of residual solvent.

Residual solvent before passing humidified gas: Ethanol: 3.0-5.0%; Isopropanol: 0.5-1.0%.

Residual solvent after passing humidified gas: Ethanol: Less than 0.5%; Isopropanol: Less than 0.5%.

EXAMPLE-8

Preparation of Imipenem Monohydrate Sterile

To purified water (255 mL) containing sodium chloride (7.5 g) was added Imipenem monohydrate (10 g) at 57-59° C. stirred to get clear solution. The clear solution was cooled to 2-10° C. and the pH was adjusted to 7.0 to 7.2 using N-methylmorpholine. methylmorpholine. To the clear solution was added carbon (3 g). Carbon was filtered and the bed washed with water. The filtrate was filtered through 0.2 micron filter paper and seeded with Imipenem monohydrate (optionally added EDTA, Sodium hydrosulphite) and acetone (or ethanol) was added slowly (alternatively the aqueous solution was added to acetone). The crystallized product obtained was filtered, washed with aqueous acetone (20 mL) followed by acetone (20 mL) and dried to give Imipenem monohydrate. (Purity: 99.35%).

We claim:

1. A process for the preparation of a sterile monohydrate of Imipenem of formula (I):

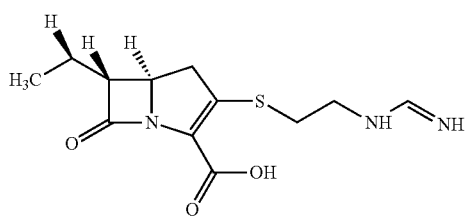

the process comprising the steps of:
i) dissolving Imipenem or its hydrate in water in the presence of inorganic salt selected from the group consisting of sodium chloride, potassium chloride, lithium chloride and mixtures thereof;
ii) optionally adjusting the pH of the step (i) solution to 6.5-7.8;
iii) treating the solution with carbon and/or decolorizing agent selected from the reagent consisting of silica, alumina, or clay;
iv) optionally filtering the solution through a micron filter
v) optionally seeding with Imipenem monohydrate;
vi) adding an organic solvent; and
vii) isolating crystalline Imipenem monohydrate.

2. The process according to claim 1, wherein the inorganic salt is sodium chloride.

3. The process according to claim 1, wherein the pH of the step (ii) solution is adjusted using a base selected from N-methylmorpholine, sodium bicarbonate, triethylamine, N,N-diisopropylamine, TMG, N-methypyrrolidine, or sodium hydroxide solution.

4. The process according to claim 1, where in the organic solvent used in step (vi) is selected from the group comprising methanol, ethanol, n-propanol, isopropanol, acetone, methyl ethyl ketone or mixture(s) thereof.

5. The process for the preparation of sterile Imipenem monohydrate according to claim 1, comprising the steps of:
i) dissolving Imipenem monohydrate in water in the presence of sodium chloride;
ii) optionally adjusting the pH of the step (i) solution to 6.5-7.8;
iii) treating the solution with carbon;
iv) optionally seeding with Imipenem monohydrate;
v) adding an organic solvent; and
vi) isolating crystalline Imipenem monohydrate.

* * * * *